US00PP31280P2

(12) United States Plant Patent
Hansen

(10) Patent No.: US PP31,280 P2
(45) Date of Patent: Dec. 24, 2019

(54) ***BRUNNERA MACROPHYLLA* PLANT NAMED 'STERLING SILVER'**

(50) Latin Name: ***Brunnera macrophylla* (Adams) I. M. Johnston**
Varietal Denomination: Sterling Silver

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,926

(22) Filed: Feb. 1, 2019

(51) Int. Cl.
*A01H 5/02* (2018.01)
*A01H 6/00* (2018.01)

(52) U.S. Cl.
USPC ..... Plt./412

(58) Field of Classification Search
USPC ..... Plt./263.1, 412
See application file for complete search history.

*Primary Examiner* — Matthew R Keogh
*Assistant Examiner* — Karen M Redden

(57) ABSTRACT

The new and distinctive cultivar of *Brunnera* plant named 'Sterling Silver' with large leaves of silver with thin dark green around the veins. The flowers are light blue flower for about four weeks in the spring. The new plant is tolerant of high temperatures.

2 Drawing Sheets

Botanical classification: *Brunnera macrophylla* (Adams) I. M. Johnston.

Variety denomination: 'Sterling Silver'.

STATEMENT REGARDING PRIOR DISCLOSURES UNDER 37 CFR 1.77(b)(6)

The first public disclosure of the claimed plant, in the form of a photograph and a brief description appeared on a website operated by Walters Gardens, Inc. on Feb. 1, 2018. The claimed plant was first sold on Oct. 22, 2018 by Walters Gardens, Inc., who obtained the plant and all information relating thereto, from the inventor. No plants of *Brunnera* 'Sterling Silver' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

*Brunnera macrophylla* is a hardy, herbaceous, sub-alpine perennial native to eastern Asia, western Caucasus and Mediterranean Europe. It has many common names, among them: Heartleaf *Brunnera*, Siberian Bugloss, and Perennial Forget-me-not.

The new and distinct *Brunnera macrophylla* 'Sterling Silver', hereinafter also referred solely by the cultivar name 'Sterling Silver' and "the new plant," is a new and unique seedling hybridized by the inventor on May 15, 2015 The female parent is a proprietary selection of 'Alexander's Great' U.S. Plant Pat. No. 25,789 times 'Alexander's Great'. The male parent is 'Diane's Gold' (not patented). The new plant passed initial evaluation in the fall of 2016 and was assigned the breeder code 15-9-8 through the remaining evaluation process until given a cultivar name. 'Sterling Silver' has been asexually propagated by sterile tissue culture propagation of the shoot tips, at the same nursery in Zeeland, Mich. since fall of 2016. The asexually produced plants are identical to the original plant, and maintains those unique characteristics in subsequent generations.

BRIEF DESCRIPTION OF THE PLANT

*Brunnera macrophylla* 'Sterling Silver' is distinct from all other Heartleaf *Brunnera* known to the inventor. 'Jack Frost' U.S. Plant Pat. No. 13,859 has similar coloration, but the amount of silver covering the leaf is less, the green surrounding the leaf veins is greater in comparison, and the foliage is smaller in size. 'Looking Glass' U.S. Plant Pat. No. 17,829 has similar amount of silver covering the leaf, but the size is smaller, the quality is lower and the plant heat tolerance is less. The female parent, has more green and less silver in the leaves. The male parent has yellow green foliage without any silver covering between the veins. 'Sea Heart' U.S. Plant Pat. No. 24,684 has more green surrounding the veins and less silver between the veins than the new plant. 'Silver Heart' U.S. Plant Pat. No. 24,685 has smaller foliage.

*Brunnera* 'Sterling Silver' differs from all other Heartleaf *Brunnera* in the following repeatedly observed trait combination:

1. Plants of compact, clumping, winter-hardy, perennial habit;
2. Foliage without a stem, held up on stiff petioles;
3. Leaf blade color is silver between the veins with narrow dark green surrounding the veins;
4. Leaf size is large;
5. Plant is tolerant of high temperatures.

BRIEF DESCRIPTION OF THE DRAWINGS

The photographs of the new invention demonstrate the overall appearance, including the unique traits, of a two-year-old plant growing in a partially shaded trial garden in Zeeland, Mich. The colors are as accurate as reasonably possible with color reproductions. Variation in ambient light spectrum, source and direction may cause the appearance of slight variation in brightness, saturation and hue.

DETAILED DESCRIPTION OF THE PLANT

Figure 1:
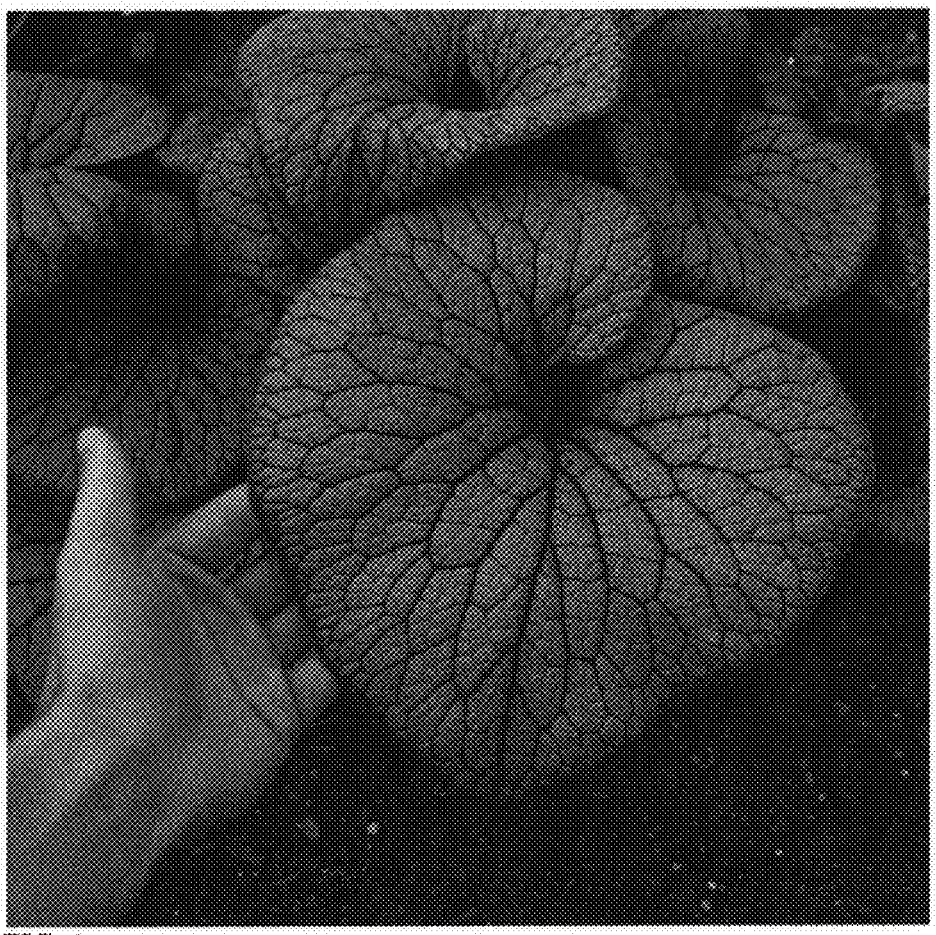
FIG. 1 shows a close-up of a leaf in early summer foliage.
Figure 2:
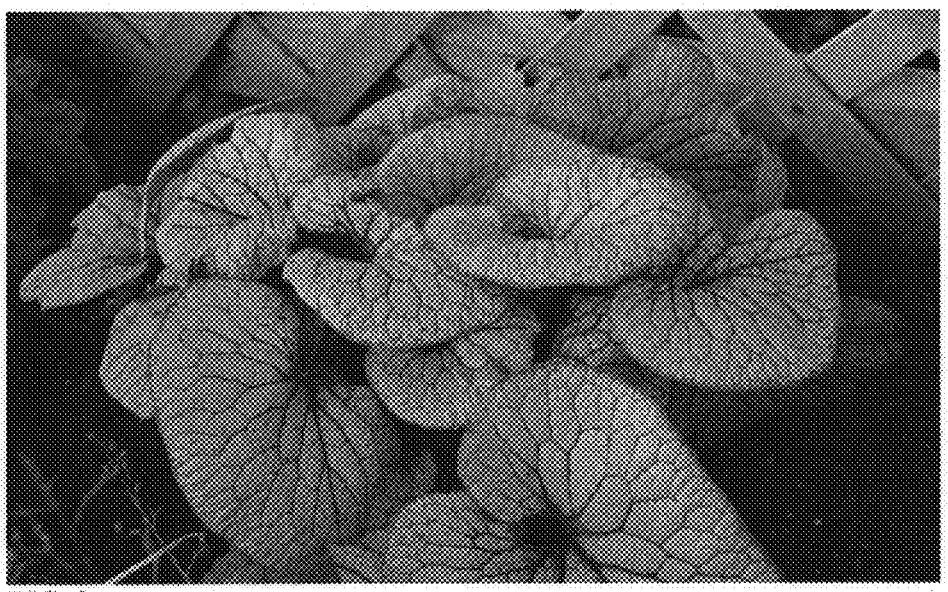
FIG. 2 shows the plant in the landscape in early summer foliage.
Figure 3:
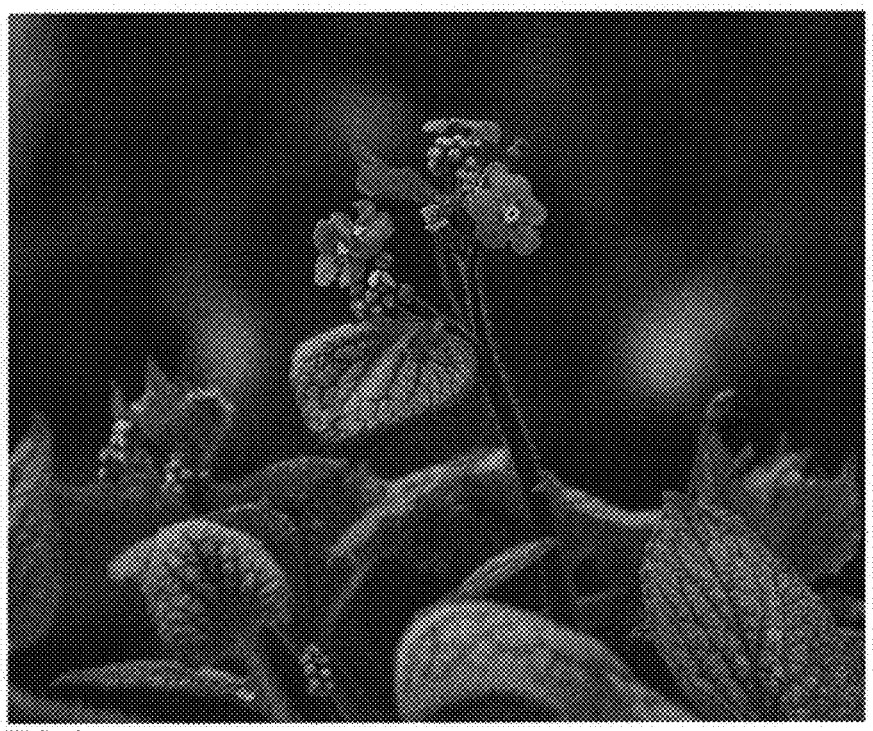
FIG. 3 shows a close-up of the flowers and buds.

The following descriptions with generic dictionary color usage are of a two-year-old plant growing in Zeeland, Mich. For more precise color descriptions the 2015 edition of The Royal Horticultural Colour Chart and the corresponding color references are used. The new plant has not been evaluated in all possible growing environments. The phenotype may vary slightly with different conditions such as fertility, light, moisture and temperature, however the genotype remains stable.

Plant habit: Winter-hardy, mounded, domed-shaped, herbaceous perennial of acaulescent foliage and with panicles in spring; foliage to 40.0 cm tall and 60.0 cm wide.

Leaves: Reniform to cordate; apex broadly acute; base cordate with lobes frequently imbricate; margin ciliolate; blade flat without undulations; adaxial and abaxial puberulent to hirsutulous; 15.0 to 25.0 cm long and 15.0 to 25.5 cm in width;

Leaf color: Adaxial surface nearest RHS 137A to about 2.0 mm surrounding major veins and the margin 3.0 mm of leaf, silver portion between veins lighter than RHS 192D or RHS 190D; abaxial surface between RHS 146B and 146C;

Petioles: Pubescent, 3.5 mm wide and up to 30 cm long; distally nearest RHS 146C and proximally nearest RHS 77A;

Venation: Reticulate; impressed and glabrous adaxial, costate and hirsutulous abaxial;

Vein color: Adaxial main and secondary nearest RHS 146C, abaxial nearest RHS 146D;

Inflorescence: Paniculate cyme with cauline leaves; about 150 flowers; to about 50.0 cm tall and 12.0 cm wide, flowering in distal 20.0 cm;

Flower buds about one to two days prior to opening: Ellipsoidal; rounded apex and slightly attenuate base; to about 3.0 mm long and 2.0 mm diameter near apex;

Flower bud color: Exposed petals nearest RHS 92D with petal margins intensified to nearest RHS 92B; sepals nearest RHS 143D;

Flower lasting: Inflorescence remaining in effective flower for about four weeks, each flower persists up to one week;

Flower timing: Beginning late April and continuing for about four weeks;

Flower: Perfect; complete; actinomophic; rotate; forming five lobed corolla with center corona; about 7.0 mm diameter and corona eye about 2.0 mm tall and 1.5 mm across;

Petals: Typically five; rounded apex, truncate fused base; margin entire; to about 3.0 mm long and 2.0 mm wide;

Petal color: Adaxial mature face nearest RHS 104B with corona nearest RHS 158A, abaxial nearest 108 D; adaxial young face between RHS 104B and RHS 104A with corona nearest NN155D, abaxial nearest RHS 100C;

Sepals: Five; forming campanulate calyx; lanceolate; narrowly acute apex; fused in basal 0.7 mm; entire margin; about 1.5 mm long and about 0.5 mm across;

Sepal color: Nearest RHS 138B;

Peduncles: Cylindrical; pubescent to hirsutulous; erect; with cauline leaves; to about 50.0 cm and to 4.0 mm diameter;

Peduncle color: Nearest RHS 138B with undertone of nearest RHS 77A or RHS 187A;

Pedicels: Cylindrical; finely puberulent; mostly upright; to about 5.0 mm long and 1.0 mm diameter;

Pedicel color: Nearest RHS 138B with undertone of nearest RHS 187A;

Androecium: Five; fused to inner corona;

*Filaments*.—Cylindrical; about 1.0 mm long; color nearest RHS NN155D.

*Anther*.—Ellipsoidal: about 1.0 mm long and 0.5 mm diameter; basifixed; color nearest RHS 155A.

*Pollen*.—Nearest RHS 155A.

Gynoecium: One; about 1.2 mm long;

*Style*.—Short, cylindrical; about 0.5 mm long; color nearest RHS 145C.

*Stigma*.—Globose; about 0.2 mm diameter; color nearest RHS 145C.

Seeds: Small nutlet; enclosed within calyx; one to four per flower; about 0.5 mm diameter; color nearest RHS 202A;

'Sterling Silver' is winter-hardy to USDA zone 3, tolerates late spring frosts, and persists after fall frosts. The new plant has no susceptibility or tolerance to pests and diseases except that which is common to *Brunnera*. 'Sterling Silver' performs best in light shade, with ample moisture, and good drainage. It is also well suited for growing in the landscape as a specimen plant, en mass, or in containers. 'Sterling Silver' is less prone to leaf scorch than 'Variegata' (not patented) and is more tolerant of high temperatures than 'Looking Glass'.

I claim:

1. A new and distinct perennial Heartleaf *Brunnera* plant named 'Sterling Silver' as herein described and illustrated.

* * * * *